United States Patent
Selim

(10) Patent No.: US 10,330,614 B1
(45) Date of Patent: Jun. 25, 2019

(54) METHODS AND SYSTEMS FOR TESTING LUMINESCENT SEMICONDUCTORS

(71) Applicant: Farida Selim, Perrysburg, OH (US)

(72) Inventor: Farida Selim, Perrysburg, OH (US)

(73) Assignee: Bowling Green State University, Bowling Green, OH (US)

( * ) Notice: Subject to any disclaimer, the term of this patent is extended or adjusted under 35 U.S.C. 154(b) by 430 days.

(21) Appl. No.: 15/141,808

(22) Filed: Apr. 28, 2016

Related U.S. Application Data

(60) Provisional application No. 62/153,739, filed on Apr. 28, 2015.

(51) Int. Cl.
| | |
|---|---|
| *G01N 25/00* | (2006.01) |
| *G01K 13/00* | (2006.01) |
| *G01N 25/20* | (2006.01) |
| *G01N 33/00* | (2006.01) |
| *G01N 21/63* | (2006.01) |

(52) U.S. Cl.
CPC ............ *G01N 25/20* (2013.01); *G01N 21/63* (2013.01); *G01N 33/00* (2013.01); *G01N 2033/0095* (2013.01)

(58) Field of Classification Search
USPC ................... 374/45, 141, 161, 208
See application file for complete search history.

(56) References Cited

U.S. PATENT DOCUMENTS

| | | | | |
|---|---|---|---|---|
| 6,512,385 | B1* | 1/2003 | Pfaff | G01R 15/241 |
| | | | | 324/754.23 |
| 8,747,801 | B2* | 6/2014 | Bowers | B82Y 20/00 |
| | | | | 252/301.6 S |
| 2001/0023063 | A1* | 9/2001 | Richter | G01N 33/542 |
| | | | | 435/6.11 |
| 2002/0110180 | A1* | 8/2002 | Barney | G01K 11/20 |
| | | | | 374/161 |

* cited by examiner

*Primary Examiner* — Mirellys Jagan
(74) *Attorney, Agent, or Firm* — Marshall & Melhorn, LLC

(57) ABSTRACT

Methods and systems using low temperature thermo-luminescence to measure donor ionization energies in luminescence semiconductors are described.

3 Claims, 5 Drawing Sheets

METHODS AND SYSTEMS FOR TESTING LUMINESCENT SEMICONDUCTORS

CROSS-REFERENCE TO RELATED APPLICATIONS

This application is a non-provisional of and, pursuant to 35 U.S.C. § 119(e), claims the benefit of, U.S. Provisional Patent Application Ser. No. 62/153,739 filed on Apr. 28, 2015 under 35 U.S.C. § 112(b). Application Ser. No. 62/153,739 is hereby incorporated by reference in its entirety to the extent permitted by law.

STATEMENT OF FEDERALLY SPONSORED RESEARCH

This invention was made with government support under (DMR1359523 grant) awarded by (National Science Foundation). The government may have certain rights in the invention.

FIELD OF THE INVENTION

The present invention relates to methods and systems using low temperature thermos-luminescence to measure donor energies in luminescence semiconductors and characterizing charge carriers in luminescent semiconductors.

BACKGROUND OF THE INVENTION

Technology

Light emitting diodes (LEDs) create light by combining electrons and holes in semiconductor materials. LEDs are incorporated into a broad range of general lighting applications and electronic devices. Testing the quality of exciting materials and developing new efficient materials for LEDs and display systems will continue to be important as LEDs are incorporated into additional products. Research at Bowling Green State University has led to the development of a spectrometer and associated method to characterize charge carriers in luminescent semiconductors and measure their ionization energies.

Measurement of ionization energies is critical in the design of optoelectronics and many semiconductor devices. The novel spectrometer and method are based on a thermally stimulated luminescence-based approach to measure the donor ionization energy. The approach has been demonstrated through the measurement of donor ionization energies in chemical vapor transport grown single crystals of zinc oxide.

The prototype system is easily fabricated, scalable, and compact. The system could be used in measuring donor energies in luminescent semiconductors and in thin films on conductive substrates.

Competitive Advantages

Current approaches to characterizing charge carriers and measuring ionization energies in luminescent semiconductors generally involve temperature dependent Hall-effect measurements. Unlike Hall-effect systems that are costly, the developed system is inexpensive and could be fabricated at a fraction of the cost of other systems. In addition, the method is a relatively simple technique that provides direct donor characterization and the sample shape or thickness uniformity of the semiconductor measured does not impact the measurement. More importantly, characterizing charge carriers in thin films on conductive layers is currently not feasible with the Hall-effect method because the applied current diffuses into the conductive layers and interferes with the measurements of the film.

Opportunity

The spectrometer and associated method of characterizing charge carriers in luminescent semiconductors would be useful in both testing the quality of exciting materials and developing new efficient materials for LEDs and display systems. The global LED lighting market is an attractive market that is expected to increase to over $42 billion by 2020. Growth in the market is fueled by decreasing cost, longer life span and higher efficiency LED lamps along with growing demand in newer applications.

SUMMARY OF THE INVENTION

The present invention is directed toward a method for measuring donor ionization energy of a luminescent semiconductor. The method may include the steps of: (i) uniformly exciting the luminescent semiconductor at low temperature, thereby generating charge carriers that can be freezed out (or trapped at donor and acceptor sites); (ii) stopping excitation of the luminescent semiconductor: (iii) heating the luminescent semiconductor to a temperature, thereby liberating the freezed charge carriers which interact at luminescent centers to emit light; (iv) measuring emission as a function of temperature; and (v) generating the glow curve and calculating an ionization energy of donors.

Also described is a system for measuring donor ionization energy of a luminescent semiconductor, wherein the system includes (i) a spectrophotometer with an excitation source configured to direct a radiation toward a sample, thereby inducing the sample to produce an emission and an emission detector configured to acquire a spectral luminescence of the produced emission by the sample, the spectral luminescence including a plurality of luminescence intensities at corresponding emission wavelengths or frequencies; and (ii) a computer configured to receive the acquired spectral luminescence and determine a donor ionization energy of the sample based on the dependence of luminescence intensity on the temperature and heating rate.

BRIEF DESCRIPTION OF THE DRAWINGS

The above, as well as other advantages of the present invention, will become readily apparent to those skilled in the art from the following detailed description when considered in the light of the accompanying drawings in which:

FIG. 5 shows two panels, where FIG.

5A is a perspective view of the follower and FIG. 5B shows a perspective view of the two halves of the follower separated from one another.

DETAILED DESCRIPTION OF THE PREFERRED EMBODIMENTS

Figure 1:
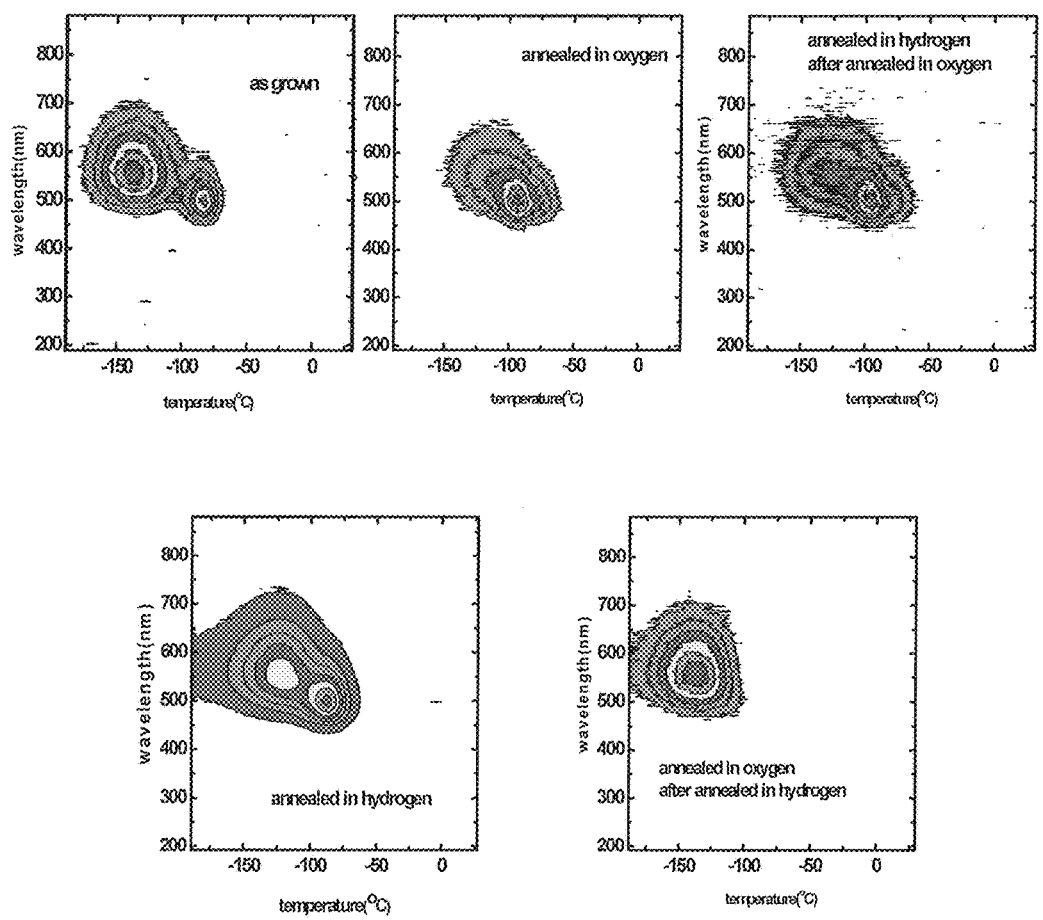
FIG. 1. Contour plots of the TL emission as a function of temperature and wavelength for ZnO single crystals grown by CVT. Measurements were carried out on as-grown and annealed samples. The heating rate was 60° C./min.

Methods and systems for using low temperature thermosluminescence to measure donor energies in luminescence semiconductors are described herein.

U.S. Pat. No. 9,261,469 issued Feb. 16, 2016 is hereby incorporated to the extent allowed by law. The '469 patent describes in more detail at least one embodiment of the spectrometer that can be used to carry out the methods and systems of the invention described herein.

Study:

The position of the transition level with respect to the valence band maximum (VBM) or conduction band minimum (CBM) corresponds to the donor/acceptor ionization energy and determines the carrier generation and both the electrical and optical properties of semiconductors.[1] Temperature-dependent Hall-effect measurements [see 2, 3, 4 and references therein] provide an effective method to measure the ionization energy—although the presence of a number of different donor or acceptor species sometimes complicates the analysis. The presence of non-uniformity in the sample thickness and shape also poses problems in carrying out the measurements. In addition, characterizing the donors in thin films on conductive layers when the applied current diffuses into the second layer of the material requires tedious work to separate this effect—if that is, indeed, possible. One recent challenging problem is represented by the case of Hall-effect measurements in the interesting $SrTiO_3/LaAlO_3$ structure.[5] An electron gas is formed at the interface of the two layers, and it is not possible to separate the effect of the layers from the interface. Other methods such as electron paramagnetic resonance (EPR)[4] and Photoluminescence (PL) have been used by Lavrov, Meyer and others[6-10] to measure the donor ionization energies, however determining the donor energy from PL measurements alone may not always be possible because of the collapse of exciton.[2]

ZnO is one of the most complex binary materials in terms of its defect and related solid-state electronic properties, and at the same time, it is an important semiconductor with both multiple existing and potential future applications.[11-21] Its properties remain a subject of controversy, and prior measurements of the donor ionization energy in ZnO samples have, in fact, shown inconsistent results in terms of the measured energies due to the many species in ZnO that may act as donors. Earlier measurements of the temperature dependence of the electrical conductivity gave a shallow donor ionization energy of 51 meV for hydrogen on interstitial sites.[22] In later experiments, however, the shallow donor energy was found to be 30 meV.[2] The activation energy obtained by EPR, on the other hand, was also found to be 35±5 meV,[4] while recent measurements have revealed another shallow donor at 47 meV.[6]

In the present work, we apply a thermally stimulated luminescence-based approach to measuring the donor ionization energy in ZnO. This method is potentially relevant for most luminescent semiconductor materials. Thermal stimulated luminescence (TSL) [also known as thermoluminescence (TL)] has been often used to measure radiation doses in solids or to examine the presence of trapping defects.[23-26] It can generally be described as follows: Uniform excitation generates charge carriers that can be trapped at lattice defects. After stopping the excitation, heating the sample to a sufficient temperature liberates the trapped electrons that can then interact at luminescence centers to emit light. From the temperature dependence of the emission, the activation energy of the traps can then be calculated. In this work, we have first irradiated ZnO single crystals with ultraviolet (UV) light at 77 K and then measured their TL emission from 77 K to room temperature. Irradiation at 77 K was sufficient to freeze out the electrons in ZnO. (Other semiconductors may, however, require irradiation at lower temperatures.) From these measurements, three hydrogen-related donors were characterized. Their ionization energies were found to be 36, 47, and 55meV—values that are consistent with the previously reported donor ionization energies in ZnO.[2-4,6-9]

High quality ZnO single crystals were grown at the Oak Ridge National Laboratory by the chemical vapor transport (CVT) method. In this process, the crystal growth is carried out via the reduction of polycrystalline spheres of ZnO that are heated to 1250° C. in an alumina tube in a mixture of flowing hydrogen and either argon or nitrogen gases. The initial interaction with hydrogen gas produces a concentration of zinc in the lower temperature region where the ZnO crystal growth will occur. Zinc vapor is formed via the reaction: $ZnO(s)+H_2(g) \rightarrow Zn(g)+H_2O(g)$. where g represents the gas phase and s represents the solid phase. A nitrogen or argon carrier gas transports the Zn vapor to a cooler region of the growth chamber where the crystals are formed by the reaction $Zn(g)+(½)O_2(g) \rightarrow ZnO(s)$ that is also accompanied by the reaction: $H_2(g)+(½)O_2(g) \rightarrow H_2O(g)$.

The resulting single-crystal ZnO samples were annealed in flowing hydrogen at 300° C. for 1 hour. Other samples were annealed in flowing oxygen at 1100° C. for 1 hour, and a few samples were annealed in both atmospheres. Annealing in $H_2$ at 300° C. will introduce hydrogen—at least into the near-surface and subsurface ZnO layers. We believe that this is sufficient for carrying out the current TL measurements, since UV irradiation only creates charge carriers in the first few layers because ZnO strongly absorbs UV light. Therefore, the effect of UV excitation should not extend into the bulk. The TSL characterization investigations were carried out using a special spectrometer that was designed and constructed in-house and that enables the direct recording of the thermo-luminescence as a function of wavelength and temperature. This spectrometer has been described in detail elsewhere.[24-26] The samples were irradiated with UV light in the dark at −190° C. (~77 k) for 30 minutes using the full power of a pulsed Xenon lamp, after which the light emission over the range of 200 to 800 nm was recorded using a charge-coupled device detector during the linear-ramp heating of the sample from −190° C. to room temperature. The heating rate for the reported measurements was 60° C./min.

FIGS. 1 (a, b, c, d and e) shows the contour plots of the TL emission as a function of temperature and wavelength for as-grown and annealed samples. The peak temperature positions change slightly with changes in the annealing atmosphere. The peak wavelength depends on the temperature and appears at both 520 and 580 nm in most of the samples. The ratio between the 580 and 520 nm emission for each sample depends substantially on the annealing atmosphere as discussed in detail below. The glow curves—which represent the luminescence intensity versus temperature—were constructed from the contour plots by integrating the luminescence intensity over the entire range of wavelengths at every temperature. These are displayed in FIGS. 2, 3, and 4 for the as-grown and annealed samples. The ionization energies can be calculated from the glow curve using two methods: either the variable-heating-rate or initial-rise methods—depending on the characteristics of the glow curve and degree of the kinetics [For a detailed description of the two methods, see Ref. 24]. The variable-heating-rate method is only applicable for the first-order kinetics whereas the initial-rise method can be used for any kinetics. We have analyzed the majority of the glow curves here using the initial-rise method[23,24] as follows. At the low temperature end of the TL peak in the glow curve, all the occupancies of the states can be considered constant. Therefore, the rise of the TL intensity as a function of temperature in this region can be expressed by the exponential relation $I(T)=C \exp(-E/K_B T)$, where E is the potential barrier (ionization energy), $K_B$ is Boltzmann constant. The constant C includes all the dependencies on the other parameters. By plotting ln (I) versus (1/T) in the low temperature region for each glow curve in FIGS. 2, 3, and 4, we obtain a straight line with the slope of $(-E/K_B)$ from which the ionization energy can be calculated directly. The only limitation of this method is that it cannot be applied for overlapping peaks.

Figure 2:
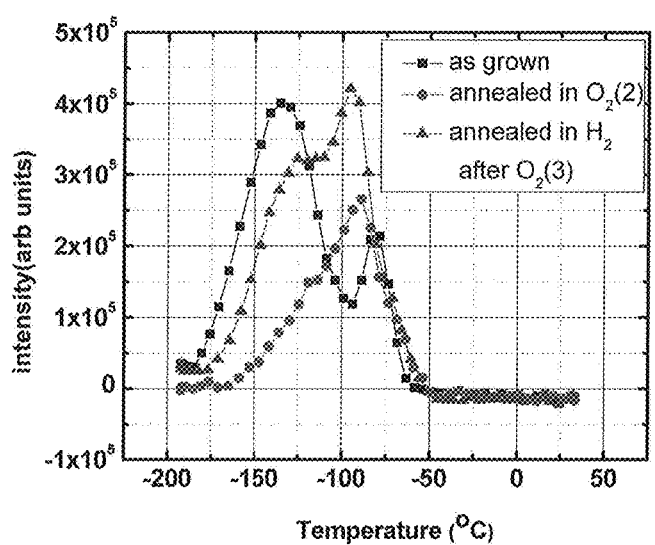
FIG. 2. TL glow curves for a ZnO single crystal grown by CVT after annealing in various atmospheres. These are constructed from the contour plots displayed in FIGS. 1 *a, b,* and *c.*

FIG. 2 displays the low-temperature glow curve for ZnO single crystals: as-grown, annealed in air, and annealed in air followed by H— anneal. The three graphs represent measurements on the same single-crystal sample after various anneals. The first peak at −135° C. in the as-grown sample was eliminated by annealing in an oxygen atmosphere—suggesting its association with oxygen vacancies. Its activation energy was calculated by the initial rise method as described above and found to be 47±3 meV. After the $O_2$ anneal, the intensity of the second peak at −89° C. increased, and a new small peak emerged at −125° C. The activation energy of this peak at −125° C. was found to be 55±5 meV. This peak has significantly increased after the $H_2$ anneal as shown in FIG. 2, and its activation energy becomes 58(4) meV. Unfortunately, it is not possible to calculate the activation energy of the second peak in the glow curves by the initial-rise method because of its overlap with the first peak. Changing the heating rate and inspecting the glow curve showed that the dynamics of the charge carriers cannot accurately be described by first-order kinetics; therefore the variable-heating-rate method also cannot be used.[24]

We assign the two ionization energies, 47 meV and 55/58 meV, to two hydrogen-related donors for the following reasons: $O_2$ anneals led to the elimination of the donors with 47 the meV ionization energy accompanied by the emergence of the donors with the 55 meV ionization energy. The 47 meV donor has been reported to be associated with $H_O$ (hydrogen bound in an oxygen vacancy) and the 55 meV donor to be associated with $H_{BC}$ (hydrogen at a bound centered lattice site),[6,7] which is consistent with the current experiment, since an anneal in $O_2$ is expected to fill the oxygen vacancies and release hydrogen as interstitials. This is why we observe a transition from 47 meV to 55 meV after the $O_2$ anneal. Subsequent anneals in hydrogen increased the H interstitials, which led to a large increase in the peak associated with the 55/58 meV energy. $H_O$ was predicted earlier from recent first-principles calculations by Janotti and Van de Wall[27] which demonstrated that a hydrogen impurity substitutes for an oxygen atom and bonds to all Zn neighbors. Subsequently, photoluminescence and photoconductivity measurements by Larvov[6,7] revealed the shallow donor nature of the $H_O$ center. The current measurements provided additional evidence for the association of the 47 meV donor ionization energy with Ho and the 55/58 meV with the $H_{BC}$ center, which has been reported to immediately appear in the IR spectra after hydrogenation.[6]

Figure 3:
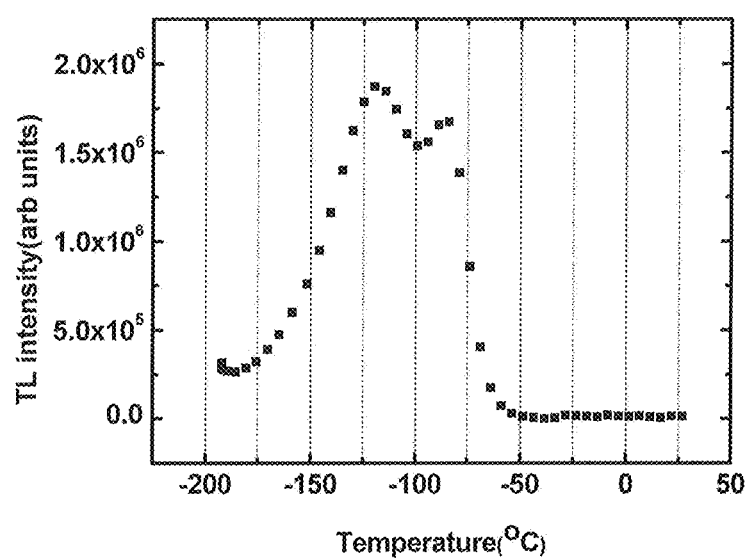
FIG. 3. TL glow curve of a ZnO single crystal grown by CVT and annealed in $H_2$ for 1 hr at 300° C. The glow curve was constructed from the contour plot displayed in FIG. 1 *d.*
Figure 4:
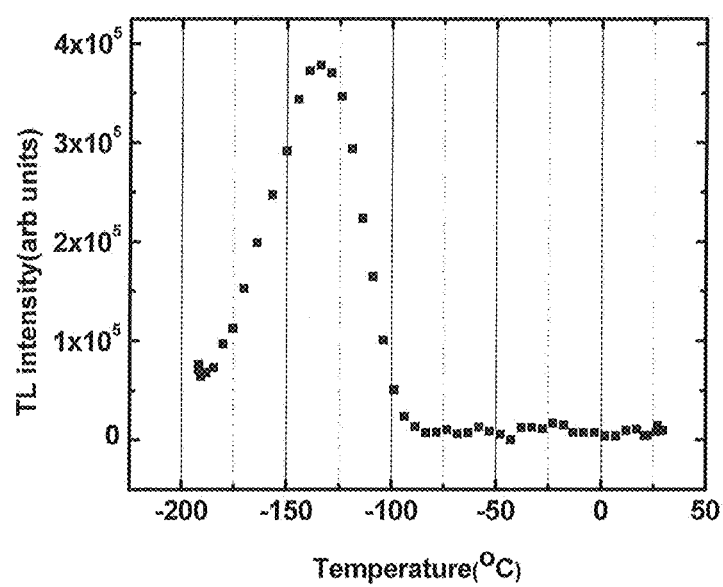
FIG. 4. TL glow curve of a ZnO single crystal grown by CVT, annealed in $H_2$ for 1 hr at 300° C., followed by annealing in $O_2$ for 1 hr at 1100° C. The glow curve was constructed from the contour plot displayed in FIG. 1 *e.*

The TL glow curve for ZnO single crystals after annealing in an $H_2$ flow for 1 hr at 300° C. is displayed in FIG. 3, and it shows two distinct peaks. The ionization energy was calculated for the first peak and was to found to be 53(1) meV, which is again consistent with the presence of $H_{BC}$ donors. FIG. 4 represents the glow curve for sample annealed in $H_2$ followed by $O_2$-anneal. Only one strong peak can be identified in the graph in this case with an activation energy of 36 meV. Table I summarizes all of the results—indicating the sample treatment, peak temperature position, activation energy value, method of calculation, and emission wavelength. The last column in Table I gives the "suggested" donor for each ionization energy based on the annealing procedure and the corresponding comparison with previous experimental and theoretical results. Three donors are identified in the Table: the 47 meV ($H_O$), 53/55/58 meV ($H_{BC}$) and the 36 meV donor. After annealing the last sample in oxygen at 1100° C., the donor with the 53 meV energy has disappeared and another donor with 36 meV has emerged. This indicates that the 36 meV value is most likely related to another hydrogen donor. This donor has been formerly reported[4] and described as being related to hydrogen; however its identity is not known. It may be associated with a negatively charged Zn vacancy passivated by a number of hydrogen atoms since high-temperature annealing has been reported to form hydrogen defect complexes.[7,17] The TL emission data discussed below also supports this interpretation.

Figure 5:
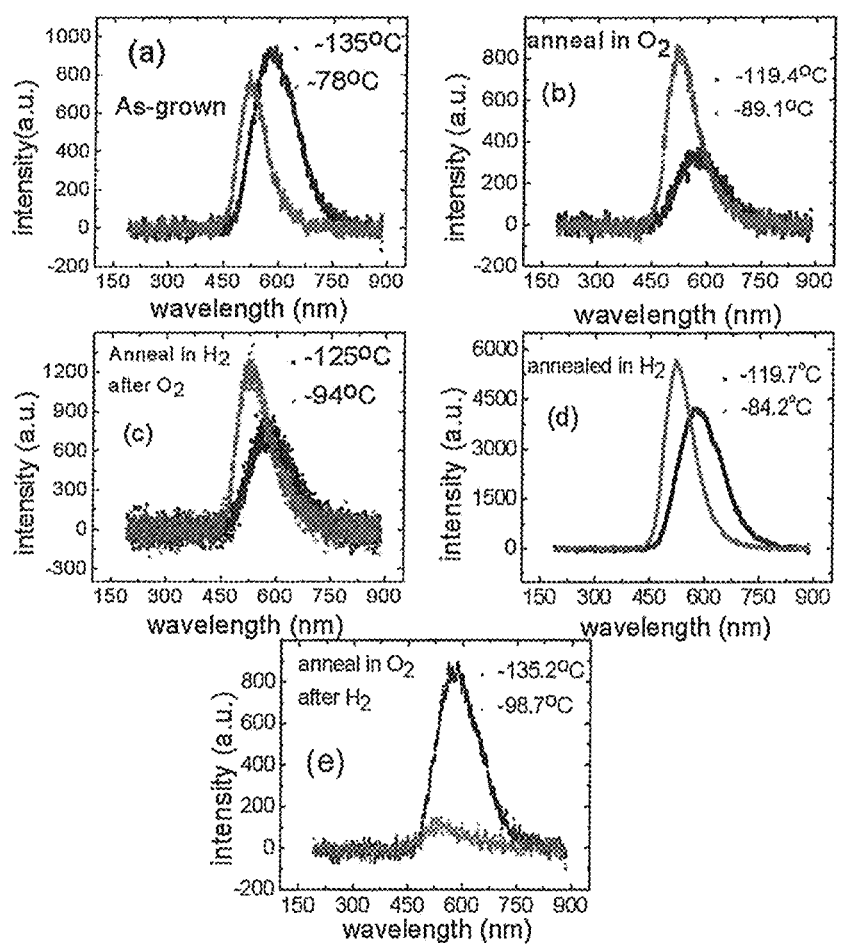
FIG. 5. Shift in the emission wavelength with temperature for as-grown and annealed ZnO single crystals. The ratio between the 580 and 520 nm strongly depends on the annealing atmosphere.

The spectral range of the TL emission from the ZnO crystals may provide new insight into the origin of the green luminescence in ZnO. The green emission from ZnO has been a controversial issue for some time, and oxygen vacancies, Zn vacancies, and impurities have all been suggested as the origin of this luminescence—with a number of publications supporting each argument.[28-35] FIGS. 5 (a, b, c, d and e) demonstrate the change of emission wavelength with temperature in the current TL measurements, and they display two distinct peaks at 580 and 520 nm for most of the samples. It can be seen from the graphs that annealing substantially changes the ratio between the 520 and 580 nm peaks. This indicates that the 520 and 580 nm emissions in ZnO are associated with different luminescence centers and that they are not due to a change in the charge state of one emission center. Recent research showed the association of the 580 nm with Zn vacancy related defects and the 520 nm with oxygen vacancy related defects [see Ref. 17 and references therein]. In the current TL measurements, $O_2$ anneal decreases the 580 nm emission (FIG. 5b), probably by filling oxygen vacancies in (Zn—O) vacancy pairs. Therefore we assign the 580 nm emission in ZnO to (Zn—O) vacancy pair. However the anneal in $O_2$ after $H_2$ anneal (FIG. 5e) has different effect; it suppresses the 520 nm emission which is expected to be associated with O-vacancies. In this case, oxygen fills oxygen vacancies instead of (Zn—O) vacancy pairs probably because of the formation of stable H—Zn Vacancy complex defects. This interpretation is consistent with the association of the 36 meV donors in this sample with Zn vacancies passivated by three or more hydrogen.

In summary, low-temperature TL spectroscopy was applied to measure the donor ionization energies in CVT-grown single crystals of ZnO, and this approach was shown to be a simple and effective characterization method. Three ionization energies have been identified and postulated to be associated with hydrogen-related donors. The measurements provide additional support for the association of the 47 meV energy with $H_O$ and the 55 meV energies with the $H_{BC}$ center, and they illustrate how annealing modifies the nature of the donor from one species to another. It is interesting to note the possibility of identifying, in the present case, these three donors in one set of measurements, since most of the previous experiments have only identified one or two types. The present measurements provide evidence for the presence of two potential emission centers for the green luminescence in ZnO that are associated with both O vacancies and Zn vacancy related defects. This donor-characterization-based TL approach provides a versatile tool for measuring donor energies in luminescent semiconductors in general, and this approach can be useful for carrying out donor studies in thin films on conductive substrates or on interfaces where Hall-effect measurements cannot provide information on charge carriers in the films. In future investigations, it may be important to extend the TL measurements from a few degrees Kelvin to room temperature to identify additional donors and to cover a wider range of ionization energies.

TABLE I

| sample | Peak position °C. | Ionization energy/eV | Calculation method | Emission peak/nm | Donor type |
|---|---|---|---|---|---|
| As grown | −135.4 | 0.0468 ± 0.0027 | Initial rise | 580 nm | $H_O$ |
|  | −78.7 | Not calculated |  | 520 nm |  |
| Annealed in $O_2$ | −119.4 | 0.05484 ± 0.005 | Initial rise | 580 nm | $H_{BC}$ |
|  | −89.1 | Not calculated |  | 520 nm |  |
| Annealed in $H_2$ after $O_2$ anneal | −125.5 | 0.05889 ± 0.0040 | Initial rise | 580 nm | $H_{BC}$ |
|  | −95.7 | Not calculated |  | 520 nm |  |
| Annealed in $H_2$ | −119.7 | 0.0528 ± 0.0008 | Initial rise | 580 nm | $H_{BC}$ |
|  | −84.2 | Not calculated |  | 520 nm |  |
| Annealed in $O_2$ after $H_2$ anneal | −134.2 | 0.0365 ± 0.0018 | Initial rise | 580 nm | Zn vacancy passivated by 3 H |

Table I. Peak positions and calculated ionization energies for as-grown and ZnO samples annealed in various atmospheres. The table shows the method of analysis, the emission wavelength that is either at 520 or 580 nm and the suggested associated donor.

REFERENCES

[1] O. Fumiyasu, First principles approaches to defect energetics in ZnO, A review, In ZnO, the future material for electronics: A comprehensive review on ZnO physics and defects, Ed: F. A. Selim (Research Signpost, Berlin, 1999).
[2] D. C. Look, J. W. Hemsky, and J. R. Sizelove, Phys. Rev. Lett. 82, 2552 (1999).
[3] D. C. Look, D. C. Reynolds, J. R. Sizelove, R. L. Jones, C. W. Litton, G. Cantwell, and W. C. Harsch, Solid State Commun. 105, 399 (1998).
[4] D. M. Hoffmann. A. Hofstaetter, F. Leiter, H. Zhou, F. Henecker, B. K. Meyer, S. B. Orlinskii, J. Schmidt, P. G. Baranov, Phys. Rev. Lett, 88, 045504, 2002.
[5] A. Ohtomo and H. Y. Hwang, Nature 427, 423 (2004).
[6] E. V. Larvov, F. Herklotz, and J. Weber, Phys. Rev. B 79, 165210 (2009).
[7] E. V. Larvov, Physica B 404, 2075 (2009).
[8] B. K. Meyer, J. Sann, D. M. Hofmann, and A. Zeuner, Semdicond. Sci. Technol. 20, S 62 (2005).
[9] B. K. Meyer, B. K. Meyer, H. Alves, D. M. Hofmann, W. Kriegseis, D. Forster, F. Bertram, J. Christen, A. Hoffmann, M. Straßburg, M. Dworzak et al., Phys. Stat. Sol. B 241, 231 (2004).
[10] A. Schildknecht, R. Sauer, and K. Thonke, Physica B 340, 205 (2003).
[11] E. Mollwo, Z. Phys. 138 (1954) 478.
[12] N. C. Giles, Chunchuan Xu, M. J. Calahan, J. S. Neal, and L. A. Boatner, Applied Physics Letters
[13] L. J. Brillson H. L. Mosbacker, b and M. J. Hetzerb, Y. Strzhemechny, G. H. Jessen, D. C. Look, G. Cantwell, J. Zhang, and J. J. SongG. Cantwell, J. Zhang, and J. J. $Song_c$, Appl. Phys. Lett, 90, 102116 (2007).
[14] E. V. Larvov, F. Herklotz, and J. Weber, Phys. Rev. Lett. 102, 185502 (2009).
[15] F. A. Selim, M. C. Taurn, D. E. Wall, L. A. Boatner, and M. D. McCluskey, Appl. Phys. Lett. 99, 202109 (2011).
[16] F. A. Selim, M. H. Weber, D. Solodovnikov, and K. G. Lynn, Phys. Rev. Letts 99, 085502 (2007).
[17] Z. Zhang, V. Quemener, C.-H. Lin, B. G. Svensson, and L. J. Brillson, Appl. Phys. Lett. 103, 072107 (2013).
[18] J. T-Thienprasert, S. Rujirawat, W. Klysubun, J. N. Duenow, T. J. Coutts, S. B. Zhang, D. C. Look, and S. Limpijumnong, Phys. Rev. Lett. 110, 055502 (2013).
[19] H. Zheng, M. Gruyters, E. Pehlke, and R. Berndt, Phys. Rev. Lett. 111, 086101(2013).
[20] L. J. Brillson, Z. Zhang, D. R. Doutt, D. C. Look, B. G. Svensson, A. Yu. Kuznetsov and F. Tuomisto, Physica Status Solidi B 250, 1953 (2013).
[21] S. G. Koch, E. V. Lavrov, and J. Weber, Phys. Rev. Lett. 108, 165501 (2012).
[22] A. R. Hutson, Phys. Rev. 108, 222 (1957).
[23] A. Bos, High sensitivity thermoluminescence dosimetry, Nucl. Instr. and Meth. in Phys. Res. B 184, 3-28 (2001).
[24] C. R. Varney, D. T. Mackay, A. Pratt, S. M. Reda, and F. A. Selim, J. Appl. Phys. 111, 063505 (2012).
[25] D. T. Mackay, C. R. Varney, J. Buscher, and F. A. Selim, J. Appl. Phys. 112, 2 (2012).
[26] S. M. Reda, C. R. Varney, and F. A. Selim, Results in Physics 2, 123 (2012).
[27] A. Janotti and C. G. Van de Walle, Nat. Mater. 6, 44 (2007).
[28] R. Dingle, Phys. Rev. Lett. 23, 579 (1969).
[29] Ya. I. Alivov, M. V. Chukichev, and V. A. Nikitenko, Semiconductors 38 (1), 31 (2004).
[39] B. Guo, Z. R. Qiu, and K. S. Wong, Appl. Phys. Lett. 82, 2290 (2003).
[31] F. K. Shan et al., Appl. Phys. Lett. 86, 221910 (2005).
[32] F. H. Leiter, H. R. Alves, A. Hofstaetter, et al., Phys. Status Solidi 226 (1), R4 (2001).
[33] M. Liu, A. H. Kitai, and P. Mascher, J. Lumin. 54, 35 (1992).
[34] D. C. Reynolds, D. C. Look, B. Jogai, J. E. Hoelscher, R. E. Sherriff, M. T. Harris and M. J. Callahan, J. Appl. Phys. 88, 2152 (2000).
[35] U. Ozgur, Ya. I. Alivov, C. Liu, A. Teke, M. A. Reshchikov, S. Doğan, V. Avrutinl, S.-J. Cho, and H. Morkoc, J. Appl. Phys. 98, 041301 (2005).

In accordance with the provisions of the patent statutes, the present invention has been described in what is considered to represent its preferred embodiments. However, it should be noted that the invention can be practiced otherwise than as specifically illustrated and described without departing from its spirit or scope.

What is claimed:

1. A system for measuring donor ionization energy of a luminescent semiconductor, wherein the system comprises:
   (i) a spectrophotometer comprising:
      (a) an excitation source configured to direct a light toward a sample, thereby creating charge carriers,
      (b) a temperature-controlled stage that can heat and cool down the sample from 77 K to room temperature,
      (c) a temperature controller for controlling the temperature-controlled stage with a variable heating rate, wherein the temperature controller is operated by software, and
      (d) an emission detector configured to acquire a spectral luminescence of a produced emission by the sample, the spectral luminescence including a plurality of luminescence intensities at corresponding emission wavelengths or frequencies; and
   (ii) a computer configured to receive the acquired spectral luminescence and determine a donor ionization energy of the sample based on the temperature dependence of luminescence intensity.

2. The system of claim 1, wherein the luminescent semiconductor comprises thin luminescent films on conducting substrates.

3. A system for measuring donor ionization energy of a luminescent semiconductor, wherein the system comprises:
   (i) a spectrophotometer comprising:
      (a) an excitation source configured to direct a light toward a sample, thereby creating charge carriers,
      (b) a temperature-controlled stage that can heat and cool down the sample from 10 K to room temperature,
      (c) a temperature controller for controlling the temperature-controlled stage with a variable heating rate, wherein the temperature controller is operated by software, and
      (d) an emission detector configured to acquire a spectral luminescence of a produced emission by the sample, the spectral luminescence including a plurality of luminescence intensities at corresponding emission wavelengths or frequencies; and
   (ii) a computer configured to receive the acquired spectral luminescence and determine a donor ionization energy of the sample based on the temperature dependence of luminescence intensity.

* * * * *